United States Patent
Knas et al.

(10) Patent No.: US 11,532,389 B1
(45) Date of Patent: Dec. 20, 2022

(54) SYSTEM AND METHOD FOR PERSONALIZED TRANSDERMAL DRUG DELIVERY

(71) Applicant: MASSACHUSETTS MUTUAL LIFE INSURANCE COMPANY, Springfield, MA (US)

(72) Inventors: Michal Knas, Monson, MA (US); Jiby John, Suffield, CT (US)

(73) Assignee: MASSACHUSETTS MUTUAL LIFE INSURANCE COMPANY, Springfield, MA (US)

( * ) Notice: Subject to any disclaimer, the term of this patent is extended or adjusted under 35 U.S.C. 154(b) by 1140 days.

(21) Appl. No.: 16/124,856

(22) Filed: Sep. 7, 2018

Related U.S. Application Data (60) Provisional application No. 62/555,273, filed on Sep. 7, 2017.

(51) Int. Cl.
  *B33Y 30/00* (2015.01)
  *B29C 64/20* (2017.01)
  (Continued)

(52) U.S. Cl.
  CPC ............ *G16H 20/17* (2018.01); *A61K 9/7023* (2013.01); *B29C 64/20* (2017.08); *B33Y 30/00* (2014.12); *A61M 37/00* (2013.01); *G16H 80/00* (2018.01)

(58) Field of Classification Search
  CPC ........ B29C 64/20; B33Y 30/00; G16H 20/17; G16H 80/00
  See application file for complete search history.

(56) References Cited

U.S. PATENT DOCUMENTS

| 4,917,676 A | 4/1990 | Heiber et al. |
| 6,110,152 A | 8/2000 | Kovelman |

(Continued)

FOREIGN PATENT DOCUMENTS

| EP | 2737891 A1 | 6/2014 |
| WO | 2009125398 A2 | 10/2009 |

(Continued)

OTHER PUBLICATIONS

Ahlam Zaid Alkilani et al, "Transdermal Drug Delivery: Innovative Pharmaceutical Developments Based on Disruption of the Barrier Properties of the stratum corneum", https://www.ncbi.nlm.nih.gov/pmc/articles/PMC4695828/>, Pharmaceutics; Oct. 22, 2015; 35 pages.

(Continued)

*Primary Examiner* — Joseph S Del Sole
*Assistant Examiner* — Mohamed K Ahmed Ali
(74) *Attorney, Agent, or Firm* — Foley & Lardner LLP (57) ABSTRACT

A transdermal delivery device for dispensing personalized transdermal dosage formulations from a plurality of reservoirs, and a personalized method for producing the transdermal delivery device. A prescription fill service receives electronic prescription data for a plurality of transdermal dosage formulations to be administered to a given patient. The prescription fill service deposits transdermal dosage formulations in two or more reservoirs of a transdermal device substrate via 3D printing of printable pharmaceutical agent. The electronic prescription data may include transdermal dosage formulations data used to select printable pharmaceutical agent deposited in respective reservoirs. The electronic prescription data further may include medication regimen data for administration of transdermal medications, such as timing data for release of selected transdermal dosage formulations. In an embodiment, a finished trans- (Continued)

dermal delivery device includes barriers formed at reservoir openings, a controller, and a controlled energy source that degrades the barriers to actuate release of reservoir contents.

12 Claims, 5 Drawing Sheets

(51) Int. Cl.
*G16H 20/17* (2018.01)
*A61K 9/70* (2006.01)
*A61M 37/00* (2006.01)
*G16H 80/00* (2018.01)

(56) References Cited

U.S. PATENT DOCUMENTS

| | | |
|---|---|---|
| 7,537,590 B2 | 5/2009 | Santini, Jr. et al. |
| 7,658,612 B2 | 2/2010 | Lee et al. |
| 8,888,480 B2 | 11/2014 | Yoo et al. |
| 9,445,762 B2 | 9/2016 | Sullivan et al. |
| 2005/0000514 A1 | 1/2005 | Sullivan et al. |
| 2006/0024358 A1 | 2/2006 | Santini et al. |
| 2007/0196456 A1 | 8/2007 | Stevens et al. |
| 2008/0274166 A1 | 11/2008 | Sacks et al. |
| 2009/0086579 A1 | 4/2009 | Clark |
| 2011/0264028 A1 | 10/2011 | Ramdas et al. |
| 2013/0193621 A1 | 8/2013 | Daya et al. |
| 2016/0263016 A1 | 9/2016 | Unger |
| 2016/0342769 A1 | 11/2016 | DeCiccio et al. |
| 2017/0100574 A1 | 4/2017 | Wei |
| 2018/0029258 A1* | 2/2018 | Okano .............. A61K 9/0021 |

FOREIGN PATENT DOCUMENTS

| | | |
|---|---|---|
| WO | 2013142339 A1 | 9/2013 |
| WO | 2016083665 A1 | 6/2016 |
| WO | 2016102284 A1 | 6/2016 |
| WO | 2017007546 A1 | 1/2017 |

OTHER PUBLICATIONS

B.W. Barry, "Novel mechanisms and devices to enable successful transdermal drug delivery", European Journal of Pharmaceutical Sciences; Jun. 14, 2001; 14 pages.

Dominic Basulto, "Why it matters that the FDA just approved the first 3D-printed drug", Washington Post; <https://www.washingtonpost.com/news/innovations/wp/2015/08/11/why-it-matters-that-th> . . . ; Aug. 11, 2015; 3 pages.

Craig L. Beylor et al., "Thermal Decomposition of Polymers", SFPE Handbook of Fire Protection Engineering 2, Section 1, Chapter 7; May 8, 2015; 22 pages.

M. Begoña Delgado-Charro et al.; "Transdermal Drug Delivery"; Drug Delivery and Targeting for Pharmacists and Pharmaceutical Scientists, Chapter 8; Francis & Taylor Group; copyright 2001; 26 pages.

Jonathan Goole et al., "3D printing in pharmaceutics: A new tool for designing customized drug delivery systems", International Journal of Pharmaceutics 499 (2016) 376-394; <http://dx.doi.org/10.1016/j.ljpharm.2015.12.071>, Jan. 3, 2016; 19 pages.

James Norman et al., "A new chapter in pharmaceutical manufacturing: 3D-printed drug products", Advanced Drug Delivery Reviews 108 (2017) 39-50, Mar. 18, 2016; 12 pages.

Thomas Rades et al., Pharmaceutics—Drug Delivery and Targeting, "Controlling drug delivery", Chapter I, Pharmaceutical Press; published Oct. 16, 2009; 24 pages.

Marian Segal, "Patches, Pumps and Timed Release: New Ways to Deliver Drugs", FDA Consumer magazine, <https://www.highbeam.com/doc/1G1-11410060.html>, Oct. 1991, 4 pages.

* cited by examiner

SYSTEM AND METHOD FOR PERSONALIZED TRANSDERMAL DRUG DELIVERY

CROSS-REFERENCE TO RELATED APPLICATION

The present application claims benefit of U.S. Provisional Application No. 62/555,273 filed Sep. 7, 2017, entitled SYSTEM AND METHOD FOR PERSONALIZED TRANSDERMAL DRUG DELIVERY, the entire contents of which are hereby incorporated by reference.

TECHNICAL FIELD

The present disclosure relates generally to techniques for transdermal drug delivery, and more particularly to a device for personalized transdermal drug delivery and methods for manufacturing and using such transdermal drug delivery device.

BACKGROUND

Transdermal drug delivery systems generally rely on diffusion of drug across the skin. In a typical conventional technology, the transdermal drug delivery system is in the form of a multi-layered patch that includes a backing or cover layer, a drug matrix/reservoir, a diffusion control membrane, and an adhesive layer for attaching the system to the surface of the skin. One transdermal drug delivery technology is reservoir systems. Commonly, reservoir-type transdermal devices include an enclosed reservoir of the drug, which may be liquid, and a polymeric membrane separating the reservoir from an adhesive layer.

The oral route is often the most convenient route for drug delivery. However, oral administration is often associated with variable absorption, with blood medication levels sometimes rising to toxic levels or falling to sub-therapeutic levels. Oral administration can cause side effects, such as gastrointestinal upset. Additionally, there can be problems with patient compliance in the case of oral drug administration, particularly in administration of multiple medications. When a patient has several medications, the sheer number of medications and the complexity of the medication administration schedule can cause treatments to be inadvertently missed or doubled.

Transdermal drug delivery ("TDD") is a painless method of delivering drugs by applying a drug formulation onto intact and healthy skin. The drug initially penetrates through the stratum corneum and then passes through the deeper epidermis and dermis without drug accumulation in the dermal layer.

TDD can provide a non-invasive alternative to parenteral routes of administration, thus circumventing issues such as needle phobia. A large surface area of skin and ease of access allows many placement options on the skin for transdermal absorption. Furthermore, the pharmacokinetic profiles of drugs are more uniform with fewer peaks, thus minimizing the risk of toxic side effects. For medications that are normally taken orally, transdermal delivery can eliminate factors such as pH changes and food intake that influence gastrointestinal absorption.

Another positive feature of transdermal drug delivery is improved patient compliance and acceptability of the drug therapy. TDD can improve patient compliance due to the reduction of dosing frequencies. TDD is also suitable for patients who are unconscious or vomiting, or persons who rely on self-administration.

While transdermal administration is known to improve patient compliance, transdermal delivery devices are typically designed for timed release of single medications and of standardized dosage forms. Transdermal delivery devices are not commonly used for dispensing multiple medications, nor for administering personalized medication regimes.

What is needed are method and apparatus for personalizing transdermal drug delivery for a given patient. Another goal is to provide improved transdermal delivery devices capable of administering multiple medications and varied dosage amounts. A further goal is to provide improved transdermal delivery devices capable of automatically administering multiple doses within a schedule, and capable of effecting a medication regime that is personalized for a given patient.

SUMMARY

Disclosed herein are systems and methods for transdermal drug delivery that address various objects in the production and administration of transdermal medications. In an exemplary method for producing customized transdermal devices, a control system of a prescription fill service receives an electronic prescription file for an identified patient, including electronic prescription data for one or more transdermal dosage formulations. In an embodiment, the electronic prescription data for the transdermal dosage formulations includes transdermal dosage formulations data for a plurality of transdermal medications. A 3D printer of the prescription fill service deposits printable pharmaceutical agent into two or more reservoirs formed in a transdermal device substrate, to substantially fill each of the two or more reservoirs with a respective one of the transdermal dosage formulations. In an embodiment, the printable pharmaceutical agent is selected based upon the dosage formulations data for each of a plurality of transdermal dosage formulations.

In an embodiment, after filling the transdermal device substrate with the transdermal dosage formulations, the transdermal device substrate is assembled with additional components to provide a finished transdermal delivery device. In an embodiment, additional components include a barrier at an opening of each of the two or more reservoirs, which prevents release of the transdermal dosage formulation from the respective reservoir; a controller for the transdermal delivery device; and a controlled energy source for actuating release of transdermal dosage formulations from selected reservoirs.

In an embodiment, the controlled energy source causes an actuating degradation of a respective barrier for actuating release from the selected reservoir. In an embodiment, the actuating degradation involves one or more of disintegrating the respective barrier; causing an actuating deformation of the respective barrier; causing a loss of structural integrity of the respective barrier due to a chemical reaction or a phase change; and causing a temperature-dependent change in permeability such that the respective barrier is rendered permeable.

In various embodiments, transdermal dosage formulations may include one or more of a therapeutic agent, a nutritional agent, a bioactive agent, and a diagnostic agent. In the present disclosure, transdermal dosage formulations are also called transdermal medications, pharmaceutically active agents, or simply active agents. In various embodiments, in administering a therapeutic agent or other bioactive agent, the transdermal delivery device may provide systemic administration or may provide local administration of the active agent.

In an embodiment, a given transdermal dosage formulation is a pharmaceutically active agent in pure form. In an embodiment, a given transdermal dosage formulation is a pharmaceutically active agent formulated with an excipient. In various embodiments, a given transdermal dosage formulation is a solid, liquid, semi-solid, solution, suspension, or emulsion formulation.

In an embodiment, the prescription fill service transmits to the 3D printer three dimensional location coordinates of each of two or more reservoirs that are selected to receive respective transdermal dosage formulations. In an embodiment, the 3D printer aligns model data for each of the transdermal dosage formulations with the three dimensional location coordinates to control printing of the transdermal dosage formulations.

In an embodiment, the electronic prescription file received by the prescription fill system further includes medication regimen data to control administration of transdermal dosage formulations by the transdermal delivery device. In an embodiment, the medication regimen data includes timing data for actuating release of each of the plurality of transdermal dosage formulations. In an embodiment, the timing data includes a release time entry for each of the transdermal dosage formulations, for controlling release of the transdermal dosage formulations via a software timer. In an embodiment, the timing data includes a time interval count for each of the transdermal dosage formulations, for controlling release of the transdermal dosage formulations via an interval timer.

In an embodiment, a transdermal delivery device for an identified user comprises a transdermal device substrate formed with two or more reservoirs, wherein each of two or more reservoirs is substantially filled with a respective one of a plurality of transdermal dosage formulations formed by depositing a respective printable pharmaceutical agent via 3D printing, wherein for each of the respective one of the plurality of transdermal dosage formulations the respective printable pharmaceutical agent is selected based upon transdermal dosage formulations data for the respective one of the plurality of transdermal dosage formulations in an electronic prescription file for the identified user; a plurality of barriers, each of the plurality of barriers positioned at an opening of a respective one of the two or more reservoirs, wherein each of the plurality of barriers prevents release of the respective one of a plurality of transdermal dosage formulations deposited in the respective one of the two or more reservoirs; a controller for the transdermal delivery device; and a controlled energy source for actuating release from at least one of the two or more reservoirs of the respective one of the plurality of transdermal dosage formulations that substantially fills the at least one of the two or more reservoirs.

In an embodiment, a method comprises receiving, by a prescription fill processor, an electronic prescription file for an identified user, the electronic prescription file including electronic prescription data for one or more transdermal dosage formulations; depositing via a 3D printer a printable pharmaceutical agent formulated based upon the electronic prescription data for the one or more transdermal dosage formulations, into respective reservoirs of two or more reservoirs formed in a transdermal device substrate of a transdermal delivery device, to substantially fill each of the respective reservoirs with a respective one of the one or more transdermal dosage formulations; and forming a plurality of barriers at the transdermal device substrate, each located at an opening of one of the two or more reservoirs, to prevent release of the one or more transdermal dosage formulations from the substantially filled reservoirs.

In an embodiment, a transdermal delivery device comprises a transdermal device substrate formed with a plurality of reservoirs, wherein two or more of the plurality of reservoirs are substantially filled with one or more transdermal dosage formulations formed by depositing a respective printable pharmaceutical agent via 3D printing; a plurality of barriers, each of the plurality of barriers positioned at an opening of a respective one of the two or more reservoirs, wherein each of the plurality of barriers prevents release of the respective one of a plurality of transdermal dosage formulations deposited in the respective one of the two or more reservoirs; a controlled energy source for actuating release from at least one of the two or more reservoirs of the respective one of the plurality of transdermal dosage formulations that substantially fills the at least one of the two or more reservoirs; and a controller for activating the controlled energy source.

In an embodiment a method comprises receiving, by a prescription fill processor, an electronic prescription file for an identified user, the electronic prescription file including electronic prescription data for a plurality of transdermal dosage formulations, wherein the electronic prescription data for each the plurality of transdermal dosage formulations includes transdermal dosage formulations data; transmitting to a 3D printer, by the prescription fill processor, model data for each of the plurality of transdermal dosage formulations, and reservoir location data comprising three dimensional location coordinates of each of two or more reservoirs formed in a transdermal device substrate; depositing, via the 3D printer, printable pharmaceutical agent into the two or more reservoirs formed in a transdermal device substrate by aligning the model data for each of the plurality of transdermal dosage formulations with the reservoir location data for a respective reservoir of the two or more reservoirs, to substantially fill each of the two or more reservoirs with a respective one of the plurality of transdermal dosage formulations, wherein respective printable pharmaceutical agent deposited into each of the two or more reservoirs is selected based upon the dosage formulations data for the respective one of the plurality of transdermal dosage formulations; and closing the substantially filled reservoirs with barriers impervious to the deposited printable pharmaceutical agent.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

DETAILED DESCRIPTION

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following description.

A transdermal delivery device dispenses personalized transdermal medication formulations from a plurality of reservoirs. In an embodiment, the transdermal delivery device comprises a drug-impervious substrate and a plurality of reservoirs formed in a release surface of the drug-impervious substrate. A plurality of personalized transdermal medication formulations are deposited in selected reservoirs via 3D medication printing. The transdermal medication formulations are dosage formulations that are customized or personalized for a particular patient or other user of the transdermal delivery device. As used herein, transdermal medications may include a therapeutic agent, a nutritional agent, other bioactive agent. Additionally, transdermal medications may include diagnostic agents.

The transdermal delivery device includes barriers (also herein called reservoir barriers or barrier layers) that prevent release of the transdermal medication formulations from the reservoirs, and a controlled energy source for actuating release of transdermal dosage formulation(s) from one or more of the reservoirs. In various embodiments, the controlled energy source causes an actuating degradation of one or more barrier, thereby actuating release of transdermal dosage formulation. In an embodiment, the controlled energy source includes control circuitry that delivers energy from a power source to selected reservoir(s) to actuate release of contents from the selected reservoir. In an embodiment, control circuitry is configured to actuate release of contents of the selected reservoir at a predetermined time.

In certain embodiments, simplified electrical, or electro-mechanical, mechanisms may be used to control release of a plurality of transdermal medication formulations from respective reservoirs of a transdermal delivery device. In various embodiments, a release sequence of reservoirs may be a variable sequence that is customized for transdermal delivery device and is stored by the controller for that device.

In other embodiments, a release sequence of reservoirs may be a predetermined sequence of given reservoirs, e.g., hardwired into the transdermal delivery device. In various embodiments, the release sequence is a predetermined sequence of given reservoirs, and the 3D printer is controlled to deposit a prescribed sequence of transdermal dosage formulations into given reservoirs of the transdermal device substrate in accordance with the predetermined sequence. In an exemplary embodiment, TDF-1 is deposited in reservoir A, TDF-2 is deposited in reservoir B, TDF-3 is deposited in reservoir C, etc. where TDF-N is the Nth transdermal dosage formulation to be released in sequence, and A, B, C, etc. is the predetermined sequence of reservoirs to be actuated.

For various embodiments, a counter/timer circuit or mechanism may activate release of transdermal medication formulations at fixed time intervals.

In an embodiment, reservoir barriers are formed at the release surface of a substrate over respective reservoirs via a 3D printing process. This 3D printing process may be the same or a different 3D process used to deposit transdermal medication formulations in the reservoirs. In another embodiment, reservoir barriers are formed at the release surface of a substrate over respective reservoirs via a process other than 3D printing, such as coating or lamination.

In an embodiment, the transdermal delivery device additionally includes a structure for securing the device to the skin of a patient or other user. In an embodiment, the transdermal delivery device further includes a material for transporting the pharmaceutical agent to the skin following release from one or more of the reservoirs.

In a method for producing transdermal delivery devices for dispensing a plurality of personalized dosage formulations, a control system for a prescription fill service receives electronic prescription data for a plurality of transdermal dosages. In an embodiment, a control system of the prescription fill service receives the electronic prescription data from an ePrescription system. (In the present disclosure, the control system for the prescription fill service is also called a prescription fill system). In an embodiment, the electronic prescription data includes dosage formulation information for a plurality of transdermal dosage formulations to be deposited in a transdermal delivery device personalized for a given user.

In various embodiments, transdermal delivery devices may be used both in treatment and in diagnosis of patients. In addition, transdermal delivery devices may administer nutritional aids and other bioactive substances. In various embodiments, a therapeutic agent or other bioactive agent administered by the transdermal delivery device may have a systemic effect on the patient, or may have a local effect on the patient. In an embodiment, the electronic prescription data further includes medication regimen data personalized for the given user. In an embodiment, the electronic prescription data may include predetermined times for release of given transdermal dosage formulations, e.g., within a day, number of days, or other time period for use of the transdermal delivery device.

The method further includes, for each the plurality of transdermal dosages, using 3D printing techniques to deposit printable pharmaceutical agent into a selected reservoir formed in a transdermal device substrate. In an embodiment, the deposited medication material substantially fills the selected reservoir with a respective transdermal dosage formulation, this formulation being based upon the dosage formulation data included in electronic prescription data for the respective transdermal dosage.

In an embodiment, the method for producing a personalized transdermal delivery device employs other processes besides 3D printing for assembling components of a finished device. In an embodiment, in addition to the transdermal device substrate with selected reservoirs filled with transdermal dosage formulations, the finished device includes a barrier formed at an opening of each the selected reservoirs. This barrier seals the associated reservoir to prevent release of transdermal dosage formulation. Additionally, the device may include a controller for controlling administration of transdermal medication, and a controlled energy source for actuating release of transdermal dosage formulation from one or more of the filled reservoirs.

The electronic prescription data may further include additional instructions for controlling the operation of a 3D printer in depositing a plurality transdermal dosage formulations in selected reservoirs of the transdermal device substrate. In some embodiments, the electronic prescription data may include instructions for depositing given transdermal dosage formulations in a given reservoir of the transdermal delivery device.

The electronic prescription data may include other information used in production and application of transdermal delivery devices. For example, the electronic prescription data may include limitations on release of multiple medications that may limit dispensing of different transdermal medication formulations within a given time period, or may require a minimum time interval between the times of initial release of multiple transdermal medication dosages, or other information on dosing schedule. The electronic prescription data may include application instructions for transdermal delivery devices, e.g., information on application site on the user's body, instructions for initial application, instructions for reapplication if a device falls off, and environmental considerations such as limitations on exposure to heat or water.

Figure 1:
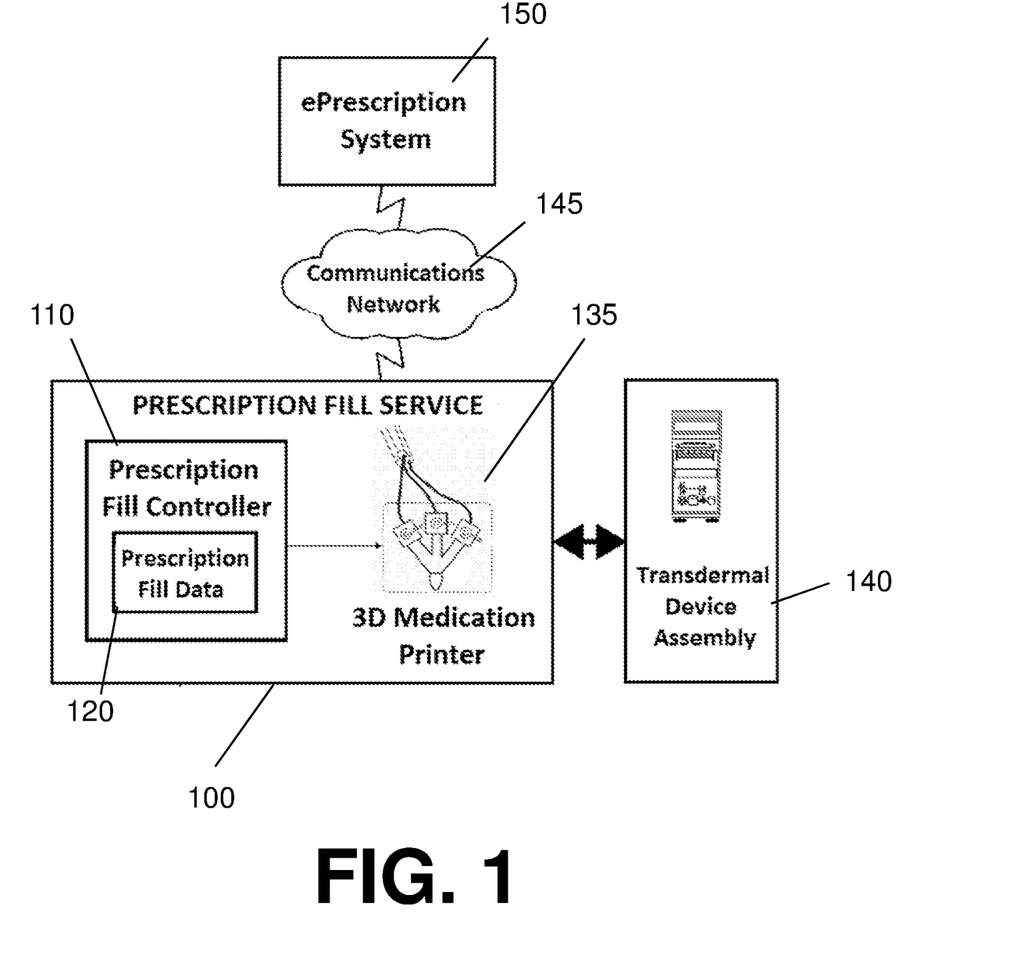
FIG. 1 is a schematic diagram of a prescription service for producing a personalized transdermal drug delivery device, according to an embodiment.

As shown in FIG. 1, a prescription fill service 100 receives electronic prescription data for a given patient from an ePrescription system 150 via communications network 145. For example, the ePrescription system may be associated with a prescribing physician or other healthcare provider. In an embodiment, the received electronic prescription data is associated with one or more prescription including a plurality of transdermal dosages to be administered to the patient via transdermal dispensing. The electronic prescription data is stored in a prescription fill database 120 and processed by prescription fill controller 110 to control production of a transdermal delivery device, personalized for the given patient in accordance with the electronic prescription data.

Electronic prescription data stored in the prescription fill controller 110 of a prescription fill service 100 is employed in controlling the operation of the 3D medication printer 150 in depositing transdermal medication formulations in selected reservoirs of a transdermal substrate for a personalized transdermal delivery device. Additionally in various embodiments, some or all of the electronic prescription data may be transmitted by the prescription fill controller 110 for storage by a transdermal device controller 200 (FIGS. 3, 5), wherein the prescription fill data is employed by the transdermal delivery device for controlling transdermal administration of the personalized medications assembled by prescription fill service 100.

Figure 2:
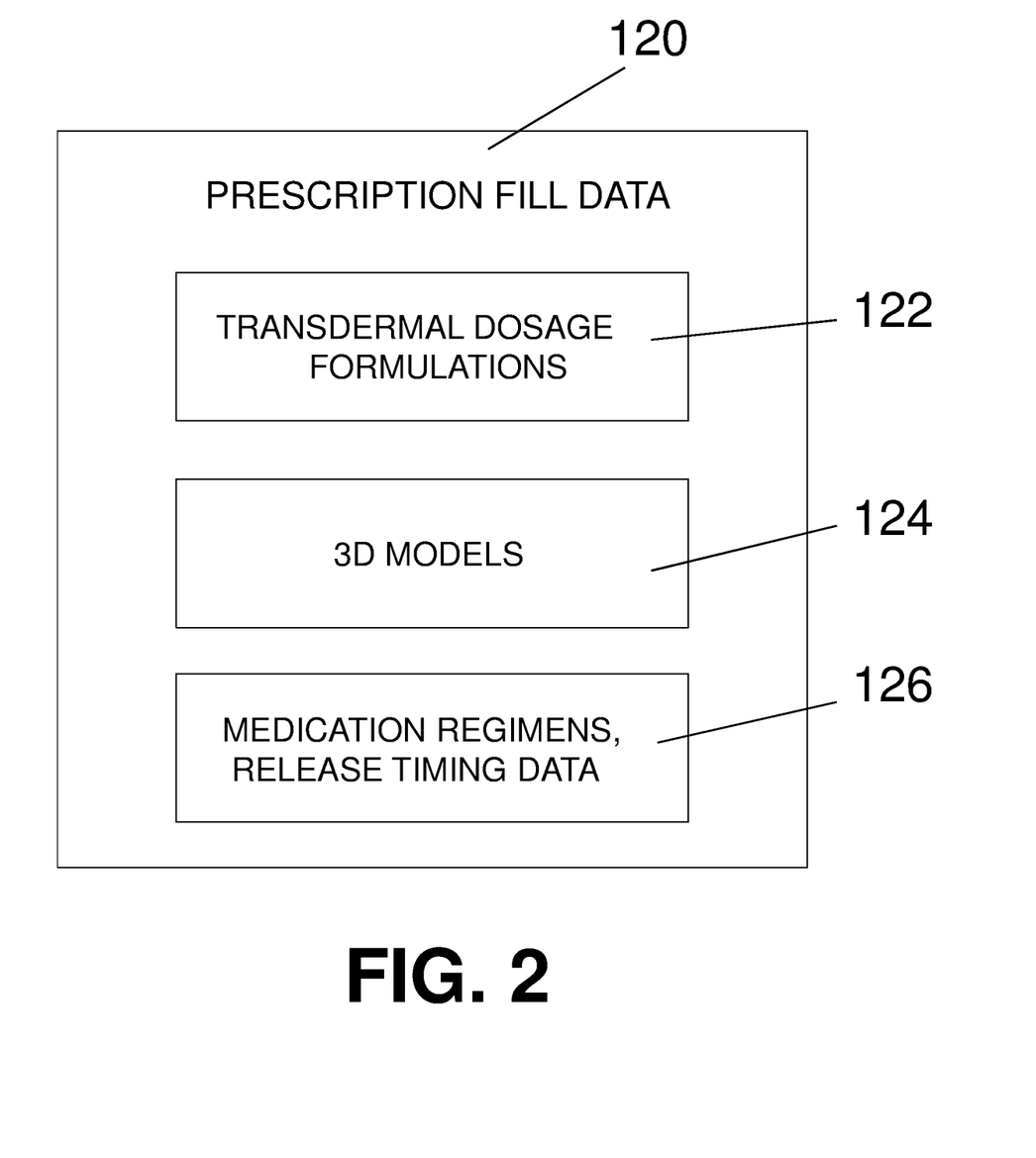
FIG. 2 is a block diagram of a prescription fill database, according to an embodiment.

In an embodiment, as seen in FIG. 2, the prescription fill database 120 of prescription service 100 may include Transdermal Dosages Formulation data 122, 3D Models data 124, and Medication Regimens/Release Timing data 126.

Transdermal Dosage Formulation data 122 includes compositional data and other information on printable pharmaceutical agent to be deposited by 3D medication printer 135 in forming a transdermal dosage formulation within a selected reservoir of a transdermal device substrate. In an embodiment, a 3D printed transdermal dosage formulation includes a composition that has an amount of pharmaceutically active agent. In some embodiments, the transdermal dosage formulation further a pharmaceutically acceptable carrier component. In various embodiments, the 3D printed transdermal dosage formulation may be a solid, liquid, semi-solid, solution, suspension, or emulsion formulation. In an embodiment, prescription fill service 100 references Transdermal Dosage Formulation data 122 in selecting printable pharmaceutical agent to be deposited in two or more reservoirs of a transdermal device substrate via 3D printer 135.

3D Models data 124 includes CAD data and/or other data using in controlling 3D printing of a given transdermal medication formulation. Dosage form designs for transdermal medication formulations can be rendered in 3D with computer-aided design (CAD) software, or in 2D as a series of images corresponding to to-be-printed layers. In an embodiment, 3D medication printer 135 includes control software that "slices" external surfaces of a 3D model 124 into distinct printable layers, and transfers layer-by-layer instructions digitally to the 3D printer. 3D models data may be included in electronic prescription data received from the ePrescription system 150; e.g., data provided by a supplier of a prescribed 3D printable transdermal medication. Alternatively, the prescription fill service 100 may store 3D models data for a plurality of 3D printable transdermal medications. In an embodiment, upon receipt of electronic prescription data for a given patient, prescription fill service 100 retrieves appropriate 3D models data from 3D Models module 124 for use in 3D printing based upon other electronic prescription data, such as brand name and/or generic dosage formulation data identifying a particular transdermal medication formulation.

In an embodiment, the prescription fill system 110 transmits to 3D printer 135 reservoir location data comprising three dimensional location coordinates of each of two or more reservoirs that are selected to receive respective transdermal dosage formulations within a coordinate system for the transdermal device substrate. In an embodiment, the 3D printer aligns model data 124 for each of the transdermal dosage formulations with the three dimensional location coordinates for the reservoir that is selected to be filled with the respective transdermal dosage formulation. In an embodiment, the transdermal device substrate may include printer registration marks or the like to align the 3D printer with a three dimensional location coordinate system for the transdermal device substrate.

Medication Regimen/Release Timing data 126 may include various electronic prescription data that provide instructions for transdermal administration of prescribed medications to the given patient. In an embodiment, Medication Regimen/Release Timing data may include predetermined times for release of given transdermal dosage formulations, e.g., within a period of usage of the transdermal delivery device. For example, timing data may include predetermined times for release of given transdermal dosage formulations within a day, number of days, or other time period. Medication regimen data can include other information, such as prescription of multiple transdermal delivery devices over an extended period of transdermal administration of medication. In an exemplary embodiment, the patient is instructed to replace a first transdermal delivery device after a certain period of use with a second transdermal delivery device, wherein both devices are produced by the prescription fill service based on the electronic prescription data. In an exemplary embodiment, a patient with a medication regimen that includes numerous transdermal dosage formulations is instructed to use multiple transdermal delivery devices daily, replace a first transdermal delivery device with a second device during the day.

Database 120 is an organized collection of data. In an embodiment, database 120 may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of database 120. The database 120 may conform to a well-known structural representational model, such as relational databases, object-oriented databases, and network databases. Exemplary database management systems include MySQL, PostgreSQL, SQLite, Microsoft SQL Server, Microsoft Access, Oracle, SAP, dBASE, FoxPro, IBM DB2, LibreOffice Base, FileMaker Pro.

In some embodiments, prescription fill controller 110 can be executed by a server, one or more server computers, authorized client computing devices, smartphones, desktop computers, laptop computers, tablet computers, PDAs and other types of processor-controlled devices that receive, process, and/or transmit digital data. The prescription fill controller 110 can be implemented using a single-processor system including one processor, or a multi-processor system including any number of suitable processors that may be employed to provide for parallel and/or sequential execution of one or more portions of the techniques described herein. Prescription fill controller 110 performs these operations as a result of central processing unit executing software instructions contained within a computer-readable medium, such as within memory. In one embodiment, the software instructions of the system are read into memory associated with the prescription fill controller 110 from another memory location, such as from a storage device, or from another computing device via communication interface. In this embodiment, the software instructions contained within memory instruct the prescription fill controller 110 to perform processes described herein. Alternatively, hardwired circuitry may be used in place of or in combination with software instructions to implement the processes described herein. Thus, implementations described herein are not limited to any specific combinations of hardware circuitry and software.

In an embodiment, the prescription fill controller 110 communicates with ePrescription system 150 via communication networks 145. Communications network 145 may employ various modes of communications such as wireless communications, wired communications, and combinations of the same. In an embodiment, prescription fill controller 110 employs a communication protocol for communication including operational instructions to communicate over the communication network 145 with ePrescription system 150. In various embodiments, prescription fill controller 110 may use any of the following communication protocols, among others: TCP-IP (Transmission Control Protocol/Internet Protocol); UDP (User Datagram Protocol); VoIP (Voice over IP); SIP (Session Initiation Protocol); Telnet; SSH (Secure Shell protocol), CAP (Common Alerting Protocol), HTTP (Hypertext Transfer Protocol), SMTP (Simple Mail Transfer Protocol), or SNMP (Simple Network Management Protocol).

In an embodiment, in addition to 3D printing 135 of transdermal dosage formulations in transdermal device substrate, the prescription fill service 100, or a manufacturing facility associated with the prescription fill service, may carry out other transdermal device assembly operations 140. Additional operations employed in the assembly of personalized transdermal devices may include, for example, adhesive coating, precision lamination, die cutting, laser cutting, assembly of functional components, and other material converting operations.

Figure 3:
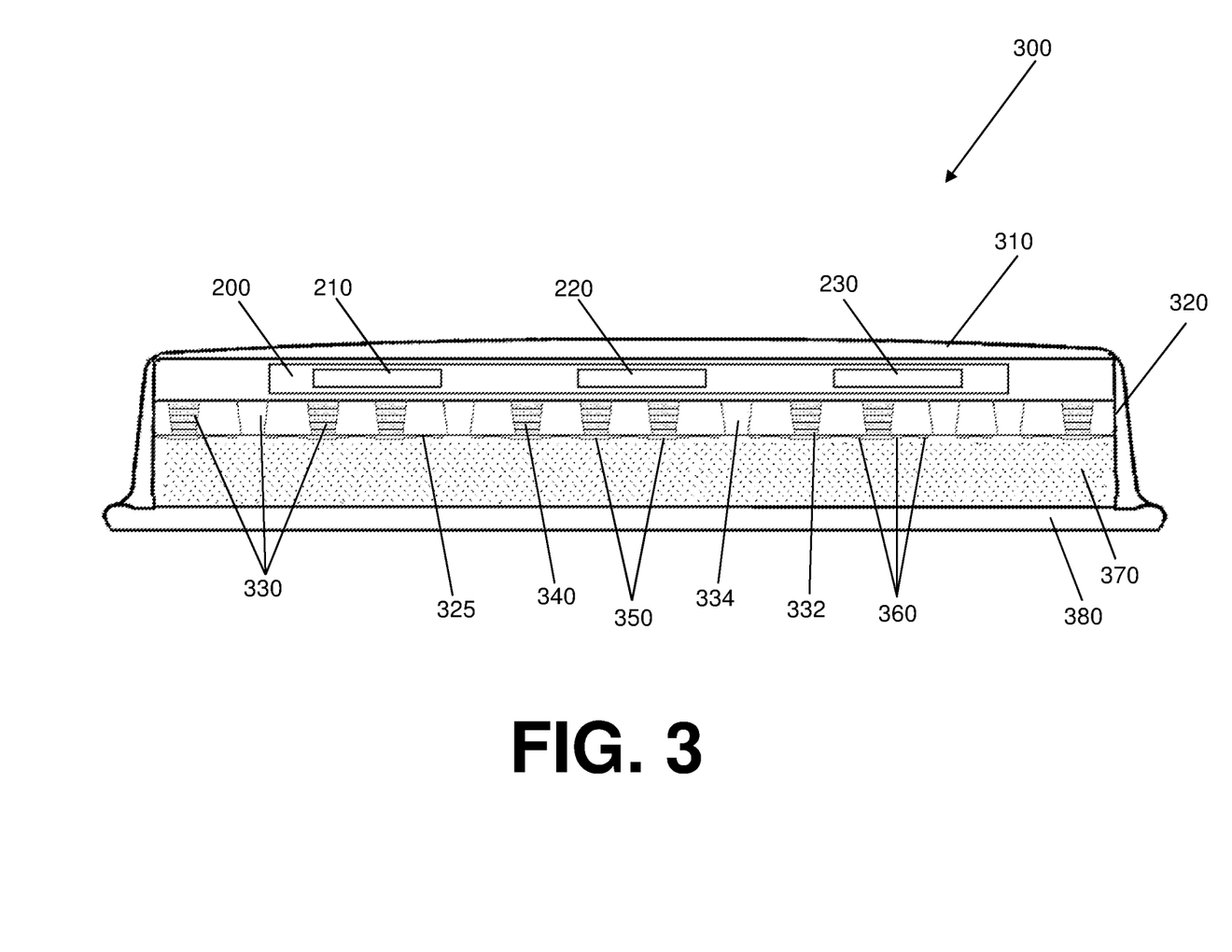
FIG. 3 is a cross-sectional view of a transdermal drug delivery device following assembly and prior to use, according to an embodiment.

FIG. 3 shows a cross sectional drawing of a personalized transdermal delivery device 300, also herein called a drug delivery patch, prior to use of that device in dispensing transdermal medications. The transdermal delivery device 300 of FIG. 3 includes a device housing 310, a controller 200 including a microprocessor 210, a communications module 220, and a power supply 230, e.g., a battery. Device 300 includes a drug-impervious substrate 320 with reservoirs 330

During customized assembly of transdermal delivery device 300, selected reservoirs 332 are filled with transdermal dosage formulations 340 by 3D printing. The selected reservoirs 332 are sealed by reservoir barriers 350, disposed at the openings of reservoirs 332 at a release surface 325 of substrate 320. In the illustrated embodiment, other reservoirs 334 do not receive transdermal dosage formulations during assembly of device 300.

Transdermal delivery device 300 also includes control circuitry 360 to control and deliver energy from the power source 330 to a selected reservoir 330 to actuate release of transdermal dosage formulations contained within the reservoir. The energy delivered by control circuitry 360 causes actuating degradation of the associated reservoir barrier 350. The illustrated embodiment includes control circuitry adjacent all reservoirs 330. In another embodiment (not shown), control circuitry is deposited on the release surface 325 of substrate 320 adjacent only the reservoirs 332 that receive transdermal dosage formulations during customized assembly of device 300.

Other layers of the assembled transdermal device 300 include a medication transport layer 370 at the release surface 325, and a permeable adhesive 380. In some embodiments, the assembled transdermal device may also include a release liner (not shown).

In an embodiment, the transdermal device substrate is a standard part used by the prescription fill service 100 in 3D printing 135. In an embodiment, the transdermal device substrate has a predetermined three dimensional configuration of reservoirs that is stored by prescription fill controller 320 and is used in conjunction with 3D models data to control 3D printing of transdermal dosage formulations in alignment with selected reservoirs. The reservoirs can be fabricated in the transdermal device substrate using fabrication techniques known in the art. Representative fabrication techniques include MEMS fabrication processes or other micromachining processes, drilling techniques, and build-up techniques. As used the present disclosure, the transdermal device substrate includes substrate 320 and may include other structures of device housing 310, but does not include layers covering the release side 325 of substrate 320 (e.g., layers 370, 380).

Figure 4:
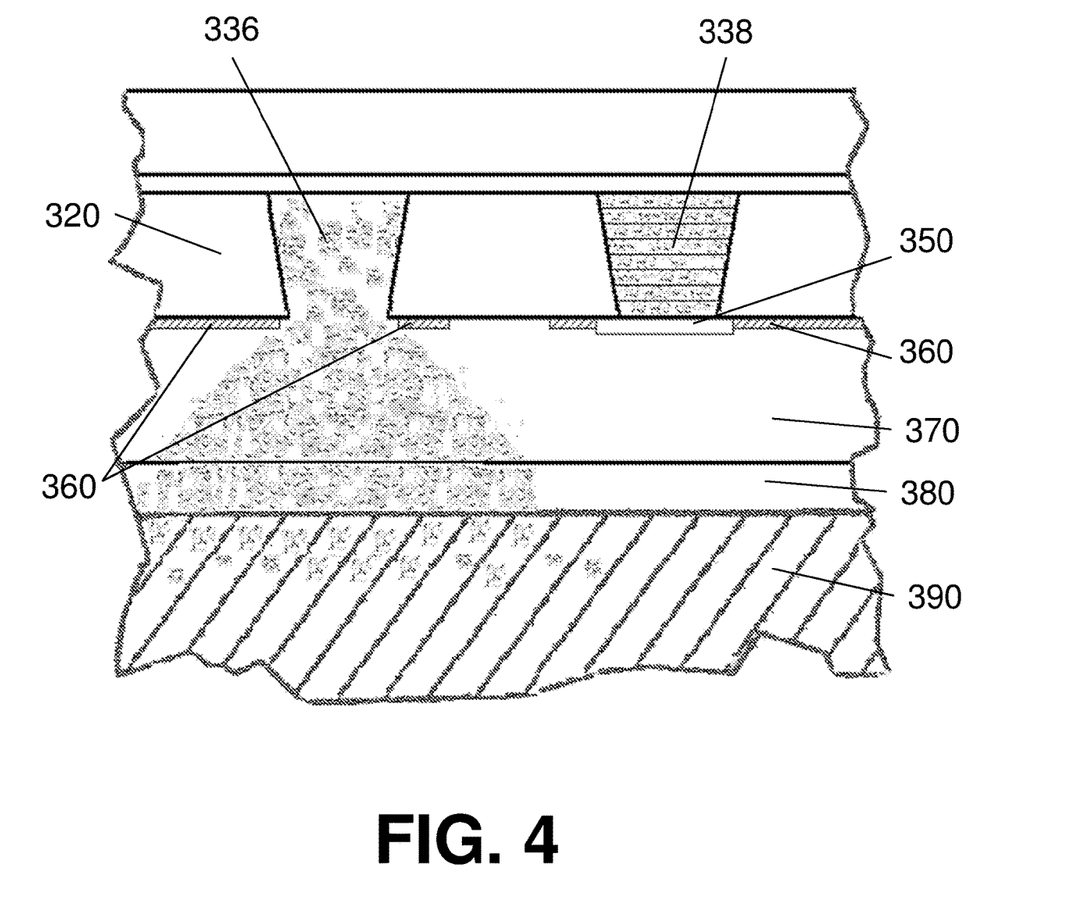
FIG. 4 is a cross-sectional view of a transdermal drug delivery device during use, according to an embodiment.

FIG. 4 shows cross sectional view of a transdermal delivery device 300 during use of that device in dispensing transdermal medications. The transdermal delivery device of FIG. 4 includes a substrate 320, a reservoir 336 with an open port, a reservoir 338 with a port sealed by a barrier 350, a medication transport layer 370, and a permeable adhesive layer 380 in contact with stratum corneum 390 layer of skin. The stratum corneum 390 is an epidermal layer of skin. The controller 200 (FIG. 2) may cause reservoir 336 in the device to open via activating degradation of the associated barrier (not shown) when a transdermal dosage formulation should be dispensed. Once the reservoir in the device opens, the medication emanates to the transport layer 370, and then flows through this layer and the adhesive layer 380 to the skin 390 (e.g., stratum corneum) of a patient. In an embodiment, controller 200 opens the reservoir based upon personalized instructions for releasing the associated transdermal dosage formulation, such as timing data, which are received by controller 200 during customized production of the transdermal delivery device 300.

In certain embodiments, the transport layer 370 controls a rate of transport of transdermal medication formulations to adhesive layer 380 following initial release of the medications from reservoirs 330. In some embodiments, the transport layer is a polymeric membrane that controls a rate of transport of transdermal medication formulations stored within reservoirs 350, while different levels of dilution of a pharmaceutically active agent in various transdermal dosage formulations can be employed to calibrate different rates of administration of respective pharmaceutically active agents by transdermal delivery device 300. In some embodiments, the rate of transfer of a drug through the transport layer 370 is slower than the rate of drug diffusion across the stratum corneum 390. In an embodiment, the adhesive layer 380 is a pressure-sensitive adhesive, which may be a solvent-free, permanently tacky, viscoelastic adhesive capable of adhering instantaneously to a variety of surfaces. In various embodiments, pressure-sensitive adhesive 380 may be an acrylate, silicone, or rubber based adhesive.

The substrate 320 can have a variety of shapes, or shaped surfaces. The substrate, for example, have a medication-release side 325 (i.e., an area including reservoir barriers, also herein called a release side or release surface of the substrate) that is planar or curved. The substrate may have various shapes, for example square, polymeric, circular, or ovoid. The transdermal delivery device may take the form of a disk including the substrate.

The substrate may consist of only one material, or may be a composite or multi-laminate structure, i.e., composed of several layers of the same or different substrate materials bonded or fused together. In one embodiment, the substrate is formed from one or more polymers, copolymers, or blends thereof. For some transdermal applications, the reservoirs need not be enclosed by hermetic materials, particularly where the time the reservoir contents are contained behind the barrier layers is relatively short, for example, when the transdermal device is a single-use device that is used only for a period of a few days.

The transdermal delivery device can be flexible or rigid. In one embodiment, the medication-release side of the finished transdermal delivery device can be shaped to conform to a curved tissue surface.

The transdermal delivery device 300 has at least two, or preferably many, reservoirs. These reservoirs are located in a plurality of identified, spaced-apart, locations within the medication-release side of the substrate. These spaced-apart locations are predetermined 2D areas within a plane representing the outer openings of the reservoirs, and the 3D configurations of the reservoirs are predetermined 3D volumes, to permit deposition of transdermal dosage formulations in precise alignment with selected reservoirs using additive manufacturing (3D printing). In various embodiments, the substrate 320 is formed with a two-dimensional array of selectively spaced reservoirs across the release surface 325.

In various embodiment, reservoirs 330 are holes or concave-shaped spaces formed in a release surface of the substrate and suitable for releasably containing transdermal medication formulations. The reservoir configuration is of a size and shape suitable for filling with a prescribed dosage amount of a transdermal medication formulation. The shape and dimensions of a reservoir can be selected to minimize contact area between the transdermal medication formulation and the surrounding surface of the reservoir, or can be selected to maximize that contact area.

In an embodiment, the surface of the reservoir optionally is treated or coated to alter one or more properties of the surface, e.g., to render the surface impermeable to transdermal medication formulations, or to provide improved release properties for transdermal medication formulations. Examples of such surface properties include hydrophilicity, hydrophobicity, wetting properties, surface roughness, release characteristics, and the like.

In some embodiments, reservoirs 330 have a microscopic volume suitable for containing small dose amounts of transdermal dosage formulations equal to or less than 500 µL (e.g., less than 100 µL, less than 20 µL, less than 5.0 µL) and greater than 10 nL (e.g., greater than 50 nL, greater than 250 nL, greater than 1.0 µL). In other embodiments, the reservoir has a macroscopic volume suitable for containing larger dose amounts of transdermal dosage formulations. For example, the volume of each reservoir can be greater than 250 µL, or greater than 1.0 mL.

In various embodiments, each of a plurality of reservoirs 330 contains a single dose of a given drug, for example for release periodically during a day or over a period of several days. In various embodiments, different reservoirs store and deliver different drug formulations from a single transdermal delivery device 300. For example, the device can contain a set of customized doses of different transdermal medications, scheduled for release at different times during a day or at different times over a period of several days, in accordance with a prescription or set of prescriptions for a given user.

As used in the present disclosure, the term "transdermal medication formulations" refers to the class of transdermal medications that have suitable properties for transdermal administration from reservoirs of a reservoir-type transdermal delivery device, and that can be formed by 3D printing. As used in the present disclosure, the term "transdermal dosage formulation" refers to a particular transdermal medication formulation deposited in a given reservoir of a personalized transdermal delivery device.

In an embodiment, components of transdermal medication formulations include a pharmaceutically active agent, such as a therapeutic agent or a diagnostic agent. In some embodiments, a pharmaceutically active agent is provided in pure form, while in other embodiments the pharmaceutically active agent is formulated with an inactive component, e.g., a carrier and/or an excipient. In various embodiments, an excipient is formulated in conjunction with the pharmaceutically active agent for properties such as long-term stabilization; or for conferring a therapeutic enhancement on the active ingredient in the final dosage form, such as facilitating drug absorption, reducing viscosity, or enhancing solubility. In some embodiments, transdermal medication formulations are formulated to control release of the drug by facilitating transport of the drug across the skin (stratum corneum).

In various embodiments, excipients may be employed for bulking up formulations that contain potent active ingredients (e.g., bulking agents, fillers, or diluents). In some embodiments, when depositing a plurality of transdermal dosage formulations in reservoirs 330 having a standard volume, the volume of pharmaceutically active agent may vary in accordance with prescribed dosage amounts, while the volume of excipient may be adjusted to provide a total volume of transdermal medication formulation that is consistent with the standard reservoir volume.

In various embodiments, transdermal dosage formulations have physiochemical and pharmacokinetic properties suitable for transdermal administration. With regard to physiochemical properties, lipophilicity and molecular size are significant determinants of stratum corneum permeability. Lipophilicity can be a key feature of drug acceptance by the stratum corneum. In an embodiment, transdermally administered active agents have log octanol-water partition in the range 0.8-3.3. Highly polar or charged substances generally are not accepted by the stratum corneum. Active agents diffusivity, in general, is size dependent, i.e., large molecules diffuse more slowly than small molecules. As for interaction between these properties, it has been observed that small polar compounds often have higher permeabilities than expected because of the importance of high diffusivity. Desirably, the pharmaceutically active agent molecule should have adequate solubility in both lipophilic and aqueous environments. These characteristics enable the drug molecule to cross the stratum corneum, a lipoidal barrier; and then transfer to viable epidermis and upper dermis, which are much more aqueous in nature.

Transdermal drug delivery systems of the present disclosure can administer a wide range of therapeutic agents. Examples include analgesics such as opioid (fentanyl and buprenorphine) and nonsteroidal anti-inflammatory drugs (NSAIDs) (diclofenac); antihypertensive drugs such as nitroglycerin (NTG); anticholinergics such as scopolamine; and other pharmaceutically active agents such as clonidine, rivastigmine, selegiline MAOI, methylphenidate, cyanocobalamin, nicotine, etc.

Additionally, the transdermal drug delivery systems can administer nutritional aids. Examples include minerals and metals, vitamins, amino acids, coenzymes, antioxidants, steroids, and hormones. Minerals and metals include boron, calcium, magnesium, chromium, selenium, zinc, etc. Vitamins include Vitamin A (Retinoids), Vitamin B1 (Thiamine), Vitamin B2 (Riboflavin), Vitamin B3 (Niacin), Vitamin B5 (Pantothenic acid), Vitamin B6 (Pyridoxine), Vitamin B7 (Biotin), Vitamin B9 (Folic acid), Vitamin B12 (Cyanocobalamin), Vitamin C (Ascorbic acid), Vitamin D2-D4 (Lumisterol, Ergocalciferol, Cholecalciferol, Dihydrotachysterol, 7-Dehydrocholesterol), Vitamin E (Tocopherol, Tocotrienol), etc. Amino acids include Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine, etc. Coenzymes include Coenzyme A, Coenzyme B12, Coenzyme Q, NAD, FAD, ATP, molybdopterin, etc. Antioxidants include Glutathione, Lutein, alpha-lipoic acid, polyphenols, Grape seed extract, superoxide dismutase, epicathechin, proanthocyanidins, sulfoxides, etc.

Common categories of steroids and steroid precursors are anabolic steroids; corticosteroids, which include glucocorticoids and mineralocorticoids; and sex steroids. Anabolic steroids interact with androgen receptors to increase muscle and bone synthesis. Glucocorticoids regulate aspects of metabolism and immune function, and are often prescribed reduce inflammatory conditions like asthma and arthritis. Mineralocorticoids help maintain blood volume and control renal excretion of electrolytes. Sex steroids are a subset of sex hormones that produce sex differences or support reproduction, and include androgens, estrogens, and progestagens. Examples of hormones include estrogen and testosterone.

An example of treatment application via transdermal administration of therapeutic agents is fatigue management, which may include dosing regimes for stimulants as well as reducing the need for a follow-up depressant to induce sleep. Another exemplary treatment application is treatment of diabetes to maintain blood glucose levels at close to normal. In an exemplary embodiment, antihyperglycemic drugs are administered via transdermal delivery to control noninsulin-dependent diabetes mellitus (NIDDM). Another exemplary treatment application is hormone replacement therapy, which seeks to restore youthful levels of hormones that decline with age (e.g., growth hormone, testosterone, estrogen, progesterone, melatonin, DHEA and thyroid). A further exemplary treatment application is obesity and weight management, in which treatments such as low-fat diet and regular exercise can be enhanced via controlled use of appetite suppressants.

An exemplary category of diagnostic applications is transdermal administration of radioactive tracers to measure glucose intake and other metabolic processes. In an exemplary application, a glucose clamp administers radiotracer labeled glucose via transdermal delivery to measure how well a patient metabolizes glucose.

The device and method of the present disclosure employs additive fabrication technologies, also referred to as three-dimensional (3D) printing, to fabrication of reservoir-type transdermal drug delivery devices. 3D printing is becoming increasingly common in product design manufacturing and design. Typically, a 3D prototype formed by an additive fabrication technology is based on what might be considered two-dimensional (2D) layers that are aggregated to form the 3D object. A digital representation of an object to be fabricated by 3D printing is constructed, for example via computer-aided design (CAD), and the digital representation can be employed to control the 3D printing process; e.g., 3D models 124.

As a digital free-form process, 3D printing can trade manufacturing tolerance for personalization. The system and method of the present disclosure uses this tradeoff in producing personalized transdermal delivery devices corresponding to given computer-stored prescriptions (ePrescription data 150), which include customized transdermal dosage formulations deposited in a plurality of transdermal device reservoirs.

The transdermal delivery devices of the present disclosure include finished dosage forms that contain an active pharmaceutical agent generally, but not necessarily, in association with inactive ingredients. 3D printing of transdermal medications generally relies on printing finished dosage forms from active pharmaceutical ingredients and excipients, rather than synthesizing substances in a step-wise, computer-controlled manner. Whether this process is called "additive manufacturing" or "3D printing", a critical distinction is that the final structure emerges from the serial addition of raw materials, largely independent of equipment or raw material geometries.

Using additive manufacturing, transdermal medication formulations can be deposited in selected reservoirs in a solid, liquid, semi-solid, solution, or suspension, or emulsion formulation. In some embodiments the transdermal medication formulation includes an inactive component, e.g., carrier and/or excipient. In various embodiments, an excipient may be selected to improve 3D printing of the transdermal medication formulation, e.g., via ink jet printing techniques.

In one embodiment, the excipient material includes a saturated drug solution. That is, the excipient material comprises a liquid solution formed of the drug dissolved in a solvent for the drug. The solution is saturated so that the solvent does not dissolve the solid matrix form of the drug. The saturated solution acts as a non-solvent excipient material, substantially filling pores and voids in the solid matrix.

Raw materials of transdermal medication formulations may be processed into granules or binder solutions to facilitate the printing process. Raw materials can be added in an automatic, layer-by-layer manner to produce the desired product.

One 3D printing technology used for pharmaceutical production is inkjet deposition on powder beds. Inkjet printers spray formulations of drugs or binders in small droplets at precise speeds, motions, and sizes onto a powder bed. Unbound powder serves as the support material for free-standing or porous structures. In some embodiments, active pharmaceutical ingredients (APIs) can be jetted onto powder beds as solutions or nanoparticulate suspensions.

In another 3D printing approach, inkjets can print free-form structures that solidify drop-by-drop. Jetted materials can include, for example, solutions, suspensions, and complex multi-component fluid. An advantage of this process in depositing transdermal medication formulations within reservoirs is resolution, as inkjet droplets are about 100 µm in diameter. Layer thicknesses for material jetting are smaller than the droplet diameter due to surface wetting, solvent evaporation, or shrinkage.

Drop-on-Drop (DoD) inkjet printing is an advantageous method for producing micro-scale dosage forms. DoD deposition is a direct-writing inkjet printing method capable of creating microscopic drug delivery systems with a range of geometries and relatively high drug loadings. In DoD 3D printing, the "printable fluid" and the building structure are the same material.

In one type of DoD 3D printing of dosage forms, a first droplet is printed containing both drug and polymer. A thermal stimulus then causes evaporation of the solvent and solidification of the polymer, allowing the deposition of a second droplet. The multi-droplets overlapping allow the construction of high-resolution three-dimensional structures. This process uses a volatile solvent that should be able to dissolve both the drug and the polymer. The printable liquid should have a suitable viscosity to avoid nozzle clogging and fluid leakage.

The transdermal delivery device of the disclosure includes components for controlling the time at which release of the transdermal dosage formulation from a given reservoir is initiated. These components include barriers 350, also herein called barrier layers or reservoir barriers, that are normally impermeable to transdermal medication formulations contained within the reservoirs. These components also include a controlled energy source for triggering mechanical degradation of the barriers at selected times.

One or more barrier layer(s) 350 associated with a given reservoir may include a membrane or other structure suitable for isolating the contents of the reservoir from the portion of the transdermal delivery device outside of the reservoir. In various embodiments, the barrier is a self-supporting layer extending across the reservoir opening. In other embodiments, the barrier may include additional structure to provide mechanical support.

In an embodiment, barriers are formed at the release surface 325 of a transdermal device substrate over respective reservoirs 330 via a 3D printing process. This 3D printing process may be the same or a different 3D process used to deposit transdermal medication formulations in the reservoirs. In an embodiment, a given barrier 350 may be formed via 3D printing over a particular reservoir 330 immediately after filling the reservoir with a transdermal dosage formulation 340. In another embodiment, a plurality of barriers 350 may be formed via 3D printing over various reservoirs 332 in a later step after all of the selected reservoirs have been filled with a transdermal dosage formulation 340. Barriers 350 formed over different reservoirs 330 may be formed with the same, or different, material.

In another embodiment, reservoir barriers are formed at the release surface 325 of a substrate over respective reservoirs via a process other than 3D printing, such as coating or lamination. In the prescription fill service 100 of FIG. 1, reservoir barriers 350 may be coated or laminated to the transdermal device substrate by transdermal device assembly after filling the selected reservoirs with transdermal dosage formulations via 3D printer 135.

In one embodiment, the controlled energy source includes control circuitry 360, including hardware, electrical components, and software to control and deliver energy from a power source to a selected reservoir. The delivered energy actuates release of contents of the selected reservoir by causing mechanical degradation of the associated barrier layer. In an embodiment, the controlled energy source delivers an electrical current to the selected reservoir. In an embodiment, the controlled energy source delivers electrical pulses to the selected reservoir. In an embodiment, the controlled energy source delivers heat to the selected reservoir, e.g., via resistive heating.

In various embodiments, application of the controlled energy source to a given barrier causes an actuating degradation of the barrier. As used in the present disclosure, actuating degradation means mechanical or other degradation of the barrier sufficient to permit the transdermal dosage formulation contained in the associated reservoir to emanate to the region of the device outside of the reservoir, also herein called release of the transdermal dosage formulation.

In various embodiments, actuating degradation may include disintegrating the barrier, e.g., via dissolving, rupturing, fracturing or some other form of mechanical failure. In an embodiments, actuating deformation includes deformation of the barrier such that at least a portion of the barrier is displaced from the opening to the reservoir to permit release of the contents. In various embodiments, actuating degradation includes a loss of structural integrity due to a chemical reaction such as electrochemical degradation, or a phase change such as melting, in response to a change in temperature. In other embodiments, actuating degradation may include a temperature-dependent change in permeability such that upon heating to a given temperature the barrier layer is rendered permeable to the transdermal medication formulation contained within the reservoir.

In certain embodiments, the barrier is formed of a conductive material through which an electrical current can be passed. The controlled energy source may include an electrical input lead and an electrical output lead operatively coupled to the barrier to permit flow of electrical current through the barrier. The controlled energy source further includes a source of electric power for applying the electrical current.

Figure 5:
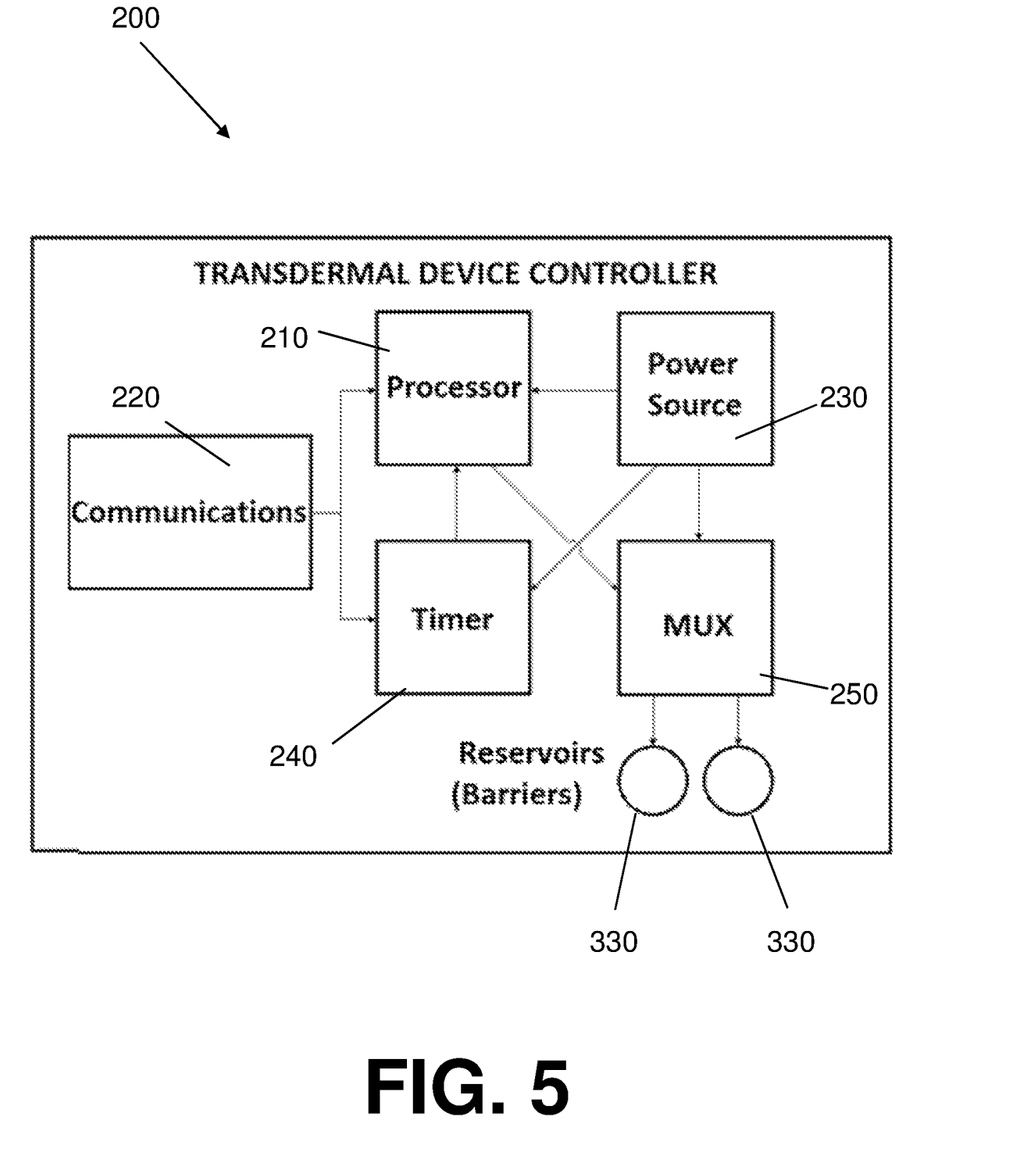
FIG. 5 is a schematic diagram of a controller for a personalized device for transdermal drug delivery, according to an embodiment.

In an embodiment shown in FIG. 5, controller 200 for transdermal delivery device 300 includes a communications module 210, a processor 220, a timer 240, a multiplexer (MUX 250), and a power source 230. The power source provides energy for actuating degradation of barriers respectively associated with one or more given reservoir(s) 330 (here, two reservoirs are shown). This controlled energy actuates release of transdermal dosage formulation(s) from the given reservoir(s). Actuating degradation can be controlled by processor 220, such as an on-device microprocessor. In various embodiments, processor 220 is programmed to initiate actuating degradation of the barriers at pre-selected times, in a selected sequence, or in some other programmed arrangement. In an embodiment, processor 220 directs power, e.g., electrical current, from power source 230 to control circuitry associated with given reservoirs 330 through a multiplexer circuit (MUX) 250. In an embodiment, flow of electrical current through barriers 350 associated with the given reservoirs disintegrates or otherwise degrades the barriers to release contents of the given reservoirs.

In various embodiments, processor 220 is programmed to effect actuating degradation of the barriers based on timing signals received from timer 240. In an embodiment, timer 240 is implemented in software, e.g., to implement a timer simulated by software built into controller 200. In an embodiment, timer 240 stores a plurality of release timing entries in a table maintained by software. In an embodiment, each of the release timing entries corresponds to release timing data 126 received from prescription fill system.

In various embodiments, a timer 240 is a timer/counter that counts intervals of time and acts as an interval timer. In these embodiments, the interval timer transmits signals at accurate time intervals (e.g., once an hour) to initiate actuating degradation of the barriers. In certain embodiments, an interval timer 240 stores interval timing data 126 received from prescription fill system, which can vary based upon electronic prescription data received from ePrescription system 150. In other embodiments, interval timer 240 stores pre-programmed data, hardwired data, or other predetermined interval data that does not vary based upon electronic prescription data received from ePrescription system 150.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method comprising:
   receiving, by a prescription fill processor, an electronic prescription file for an identified user, the electronic prescription file including electronic prescription data for one or more transdermal dosage formulations;
   depositing via a 3D printer a printable pharmaceutical agent formulated based upon the electronic prescription data for the one or more transdermal dosage formulations, into respective reservoirs of two or more reservoirs formed in a transdermal device substrate of a transdermal delivery device, to substantially fill each of the respective reservoirs with a respective one of the one or more transdermal dosage formulations; and forming via the 3D printer a plurality of barriers at the transdermal device substrate, each located at an opening of one of the two or more reservoirs, to prevent release of the one or more transdermal dosage formulations from the substantially filled reservoirs.

2. The method of claim 1, wherein the electronic prescription data comprise transdermal dosage formulations data for a plurality of transdermal dosage formulations.

3. The method of claim 1, wherein the electronic prescription data for each of the one or more transdermal dosage formulations comprise transdermal dosage formulations data and medication regimen data.

4. The method of claim 3, wherein the medication regimen data includes timing data for actuating release of the one or more transdermal dosage formulations that substantially fill the respective reservoirs of the two or more reservoirs.

5. The method of claim 1, wherein the transdermal delivery device further comprises a controlled energy source for actuating release of one or more of the one or more transdermal dosage formulations from a selected reservoir of the substantially filled reservoirs, and a controller for activating the controlled energy source.

6. The method of claim 5, further comprising the step of transmitting to the controller for the transdermal delivery device, reservoir location data specifying a three dimensional location within the transdermal device substrate of each of respective reservoir substantially filled with the respective one of the one or more transdermal dosage formulations.

7. The method of claim 6, further comprising the step of transmitting model data for each of the one or more transdermal dosage formulations to the 3D printer, wherein the step of depositing via the 3D printer printable pharmaceutical agent further comprises aligning the model data for each of the one or more transdermal dosage formulations with the reservoir location data for a respective reservoir of the two or more reservoirs.

8. The method of claim 1, wherein in the step of depositing by the 3D printer, the printable pharmaceutical agent into the respective reservoirs of the two or more reservoirs formed in the transdermal device substrate, the printable pharmaceutical agent comprises one or more of a therapeutic agent for systemic effects, and a therapeutic agent for local action.

9. The method of claim 1, wherein in the step of depositing by the 3D printer, the printable pharmaceutical agent into the respective reservoirs of the two or more reservoirs formed in the transdermal device substrate, the printable pharmaceutical agent comprises a diagnostic agent.

10. The method of claim 1, wherein in the step of depositing by the 3D printer, the printable pharmaceutical agent into the respective reservoirs of the two or more reservoirs formed in the transdermal device substrate, the selected one of the plurality of transdermal dosage formulations comprises a pharmaceutically active agent formulated with an excipient.

11. The method of claim 1, wherein the step of depositing printable pharmaceutical agent via the 3D printer comprises depositing the printable pharmaceutical agent via drop-on-drop inkjet printing.

12. A method comprising:
receiving, by a prescription fill processor, an electronic prescription file for an identified user, the electronic prescription file including electronic prescription data for a plurality of transdermal dosage formulations, wherein the electronic prescription data for each the plurality of transdermal dosage formulations includes transdermal dosage formulations data;

transmitting, by the prescription fill processor to a 3D printer, by the prescription fill processor, model data for each of the plurality of transdermal dosage formulations, and reservoir location data comprising three dimensional location coordinates of each of two or more reservoirs formed in a transdermal device substrate;

depositing, via the 3D printer, printable pharmaceutical agent into the two or more reservoirs formed in a transdermal device substrate by aligning the model data for each of the plurality of transdermal dosage formulations with the reservoir location data for a respective reservoir of the two or more reservoirs, to substantially fill each of the two or more reservoirs with the respective one of the plurality of transdermal dosage formulations, wherein respective printable pharmaceutical agent deposited into each of the two or more reservoirs is selected based upon the dosage formulations data for the respective one of the plurality of transdermal dosage formulations; and closing, via the 3D printer, the substantially filled reservoirs with barriers impervious to the deposited printable pharmaceutical agent.

\* \* \* \* \*